United States Patent [19]

Chapman et al.

[11] Patent Number: 4,544,782

[45] Date of Patent: Oct. 1, 1985

[54] THERMAL STYRENE FORMATION IN THE PRESENCE OF $O_2$

[75] Inventors: Orville L. Chapman, Los Angeles; Uh-Po E. Tsou, La Palma, both of Calif.

[73] Assignee: The Regents of the University of California, Berkeley, Calif.

[21] Appl. No.: 576,051

[22] Filed: Feb. 1, 1984

[51] Int. Cl.$^4$ .............................................. C07C 15/02
[52] U.S. Cl. .................................. 585/443; 585/435; 585/440
[58] Field of Search ............... 585/435, 436, 439, 440, 585/443

[56] References Cited

U.S. PATENT DOCUMENTS

| | | | |
|---|---|---|---|
| 1,552,875 | 9/1925 | Ostromislensky et al. | 585/439 |
| 2,110,829 | 3/1938 | Dreisbach | 585/440 |
| 2,110,830 | 3/1938 | Dreisbach | 585/440 |
| 3,396,206 | 8/1968 | Scott | 585/439 |
| 3,579,521 | 5/1971 | Franz | 585/440 |
| 3,830,853 | 8/1974 | Khcheian et al. | 585/443 |
| 3,925,496 | 12/1975 | Shalit et al. | 585/439 |

FOREIGN PATENT DOCUMENTS 0769637  1/1972  Belgium .............................. 585/443

Primary Examiner—D. E. Gantz
Assistant Examiner—Lance Johnson
Attorney, Agent, or Firm—Nilsson, Robbins, Dalgarn, Berliner, Carson & Wurst

[57] ABSTRACT

Single-stage thermolysis of $C_8$ and $C_9$ aromatics at temperatures in excess of 900° C. and pressures of less than 0.2 torr or in the presence of steam in excess of 800° C., in the absence of catalysts yields styrene and/or p-methylstyrene in high yields, providing a process for the conversion of xylenes and p-ethyltoluene to preferred styrene monomers.

7 Claims, 3 Drawing Figures

THERMAL STYRENE FORMATION IN THE PRESENCE OF O₂

FIELD OF THE INVENTION

This invention relates generally to the field of chemistry and more particularly to the thermolytic formation of olefins.

BACKGROUND AND SUMMARY OF THE INVENTION

Olefins are often formed by catalytic dehydrogenation reactions, for example, the styrene monomer is generally formed by the reaction of ethylene and benzene in the presence of aluminum chloride to yield ethylbenzene, which is then catalytically dehydrogenated at about 600° to 700° C. to form styrene. Alternatively, styrene may be formed by the chlorination of ethylbenzene and the subsequent removal of hydrogen chloride. However, these methods require substantial care and expense with regard to the elimination of by-products such as phenylacetylene and alpha-methylstyrene, each of which are particularly troublesome when present during the formation of the various styrene polymers.

Moreover, the demand for ethylbenzene is sufficient to occasion a need for a styrene-forming reaction with an alternative and less expensive starting material.

U.S. Pat. No. 2,110,830 to Dreisbach details the thermolysis of isopropyl benzene in the presence of steam at a temperature of from 750° to 950° C. for the simultaneous formation of styrene and phenylacetylene, and particularly teaches that the yield of phenylacetylene increases with the reaction temperature. The separation of the phenylacetylene from the styrene is then attained by additional purification steps, i.e., by distillation or precipitation.

U.S. Pat. No. 2,441,095 to Cheney et al., describes temperatures of from 650° to 900° C. at pressures of from about 15 to 100 psi to attain a catalytic dehydrogenation of isopropyl benzene to form styrene and alpha-methylstyrene. As noted, alpha-methylstyrene inhibits the polymerization of the various other styrenes due to the presence of the methyl group on the alpha-carbon.

Accordingly, it has been a desideratum to provide a direct process for the conversion of C₈ and C₉ aromatics to polymerizable styrenes, particularly styrene and para-methyl styrene, without the formation of by-products which interfere with further use of the product. More generally, it would be advantageous to provide a similar method for the formation of styrene and polymerizable styrene derivatives from products which are less in demand than cumene and other known starting materials, e.g., from plentiful materials such as xylenes.

According to the present invention, the gas-phase thermolysis of a variety of C₈ and C₉ aromatics gives styrene and/or polymerizable methylstyrenes in yields of up to 98% at high conversion rates. Aromatic substrates include ortho-xylene, meta-xylene, para-xylene, mixed xylenes, benzocyclobutene, cumene (isopropyl benzene), ortho-alkyltoluene, meta-alkyltoluene, para-alkyltoluene, mixed alkyltoluenes, ortho-cymene, meta-cymene, para-cymene, mixed cymenes, and functionalized derivatives thereof. These substrates include compounds which are in lower demand than the starting materials currently in use for the production of styrenes. In particular, mixed xylenes are currently the least expensive aromatic compound available, and thus is a precursor of choice if there were an economical conversion process.

Thus, C₈ and C₉ precursors in a gas-phase are thermolyzed at temperatures in excess of about 900° C. at low pressures, or in excess of about 800° C. in the presence of inert diluents or dehydrogenating vapors, in a one-step process for the formation of polymerizable styrenes.

The terms "thermolysis" and "thermolytic", as used herein, should be understood to refer to the transformation of the aromatic compound by heat alone, i.e., without oxidation in the sense of oxygen combining with the starting compound. While such a process may also be referred to as pyrolysis, we prefer the term "thermolysis" in that it literally refers to the application of heat rather than fire. Although either of these terms imply decomposition into smaller fragments, thermolytic change may also involve isomerization and the formation of higher molecular weight compounds.

DETAILED DESCRIPTION

Figure 1:
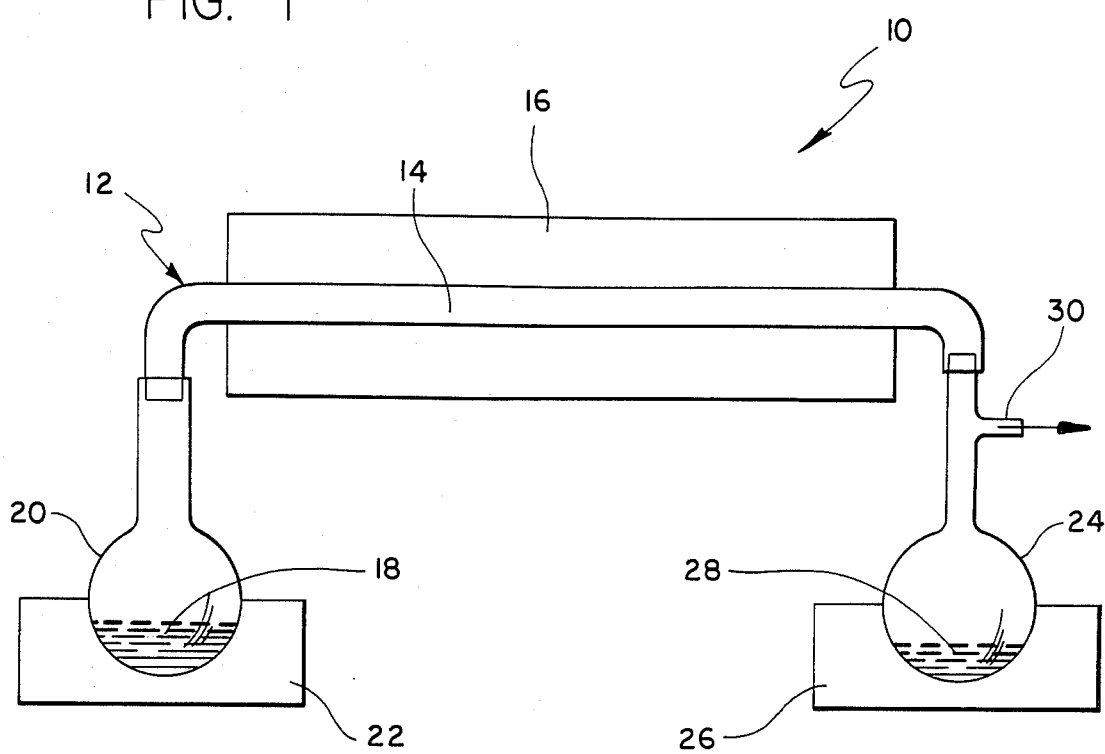
FIG. 1 is a partially schematic view, in cross-section, of an enabling apparatus for the present invention.

Details of illustrative embodiments of the invention are hereinafter disclosed. However, it is to be understood that these embodiments merely exemplify the invention, which may take forms different from the specific embodiments set forth as functional details are not necessarily to be interpreted as limiting, but rather as a basis for the claims.

While we do not wish to be bound by any particular theory, it appears that during thermolysis, carbene intermediaries tend to interreact, forming undesired products. The rate constant for such intermolecular polymerization generally proceeds as a square of the substrate pressure, while the rate constant for the desired reactions proceeds directly with such pressure. According to the procedures employed herein, intermolecular polymerization is virtually eliminated.

The aromatic starting materials may be described as aromatic compounds having the formula

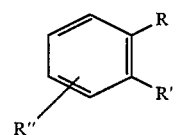

wherein R is alkyl; R' is H or alkyl, or where R and R' together form cyclobutene; and R'' is H or alkyl, and include ortho-, meta-, para- or mixed xylenes,

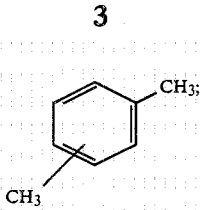

ortho-, meta-, para- or mixed ethyltoluenes,

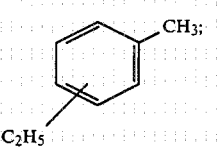

ortho-, meta-, para- or mixed cymenes,

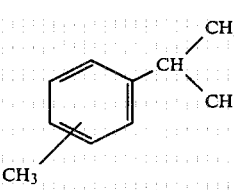

cumene (isopropylbenzene),

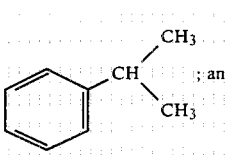

benzocyclobutene ($C_8H_8$),

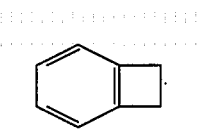

In addition, R or R' may be methyl or a higher alkyl which includes a departing group, i.e., a halogen such as chloride or an hydroxyl or other oxygen-containing leaving group, which will promote the dehydrogenation such as by forming hydrogen chloride or water. The inclusion of such a departing group will bias the equilibrium of the thermolytic reaction and lower the required temperature of the reaction to as low as 750° C.

This effect may also be caused by the inclusion of vapors which form the departing groups within the reaction zone. Small amounts of oxygen or a halogen such as chlorine are particularly useful in this regard in that they tend to prohibit reversal of the carbene-forming reaction. The amount of such departing group forming vapors should be less than that which causes any substantial interaction of the carbene intermediaries formed, so that intermolecular polymerization is limited. The addition of oxygen or chlorine vapors in amounts of up to 5% of the starting material is particularly effective for this purpose.

While the thermolytic reaction is described herein with regard to vacuum systems presenting an atmospheric pressure of less than 0.2 torr, it should be understood that the described thermolysis may also be conducted in the presence of an inert diluent such as nitrogen, carbon dioxide or preferably steam.

In the presence of such diluents, intermolecular polymerization is limited even though increased substrate pressures are employed. Moreover, the diluents provide better thermal conducting conditions and facilitate control of the flow of the substrate. Thus, the throughput of the reaction zone may be increased by the use of superheated steam in a steam-to-substrate ratio of up to about five to one, at a total pressure of up to one-half atmosphere. Procedures and apparatus for the use of steam and other diluents in thermolysis reactions are known and their use in the reactions described herein will become apparent to those skilled in the art without undue experimentation. While the thermolysis of xylene, for example, is conducted at 1000° C., the reaction may be conducted in steam at temperatures greater than 800° C., preferably about 900° C.

Turning first to FIG. 1, reactions are conducted in a conversion apparatus represented by the reference numeral 10. The apparatus 10 is seen to comprise a tube 12 which includes a reaction zone portion 14 surrounded by a furnace 16 in order to provide the described temperatures therein. The starting material 18 is seen to be contained in a vessel 20, the material 18 being vaporized by a second furnace 22. In this regard, it should be noted that the temperature of the furnace 22 is adjusted to control the flow rate of the starting material through the reaction zone 14.

The apparatus 10 is further seen to include a receiving vessel 24, partially enclosed by a cooling means 26 which assists in the condensation of an end product 28. The vessel 24 is seen to include an outlet 30 which communicates with a vacuum pump, not shown, to provide the described pressure within the apparatus 10.

Figure 2:
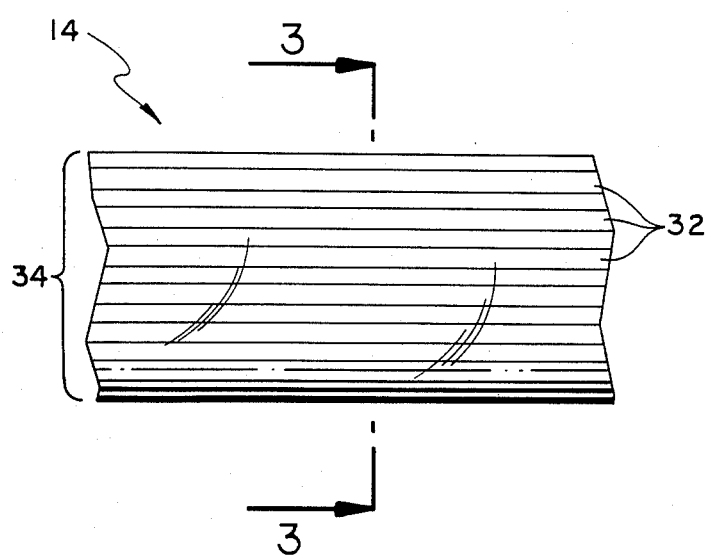
FIG. 2 is an alternative embodiment of the reaction zone 14 of FIG. 1.
Figure 3:
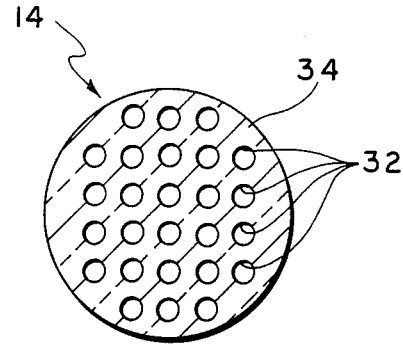
FIG. 3 is a cross-sectional view taken along the line 3—3 of FIG. 2.

The reaction zone 14 may be provided in a variety of forms and constructed of materials as are known in the art, although quartz tubing has been found to be preferable in such high temperature-low pressure systems. However, substantial advantages are presented by the use of a plurality of tubular reaction zones 32 within a core 34, such as is shown in FIGS. 2 and 3. The plurality of passages 32 allows the transport of a volume of vapor similar to that of a single, larger tube, yet provides a more even distribution of reaction temperature across the total volume of reacting vapors.

According to the process of the present invention, an appropriate starting material is placed within the vessel 20. Such starting materials include aromatic compounds such as xylenes, cymenes, toluenes and heterocyclic benzene derivatives and may include other substrates which undergo an equivalent reaction in the apparatus 10.

Prior to such reaction, the tube 12 and the vessels 20 and 24 are evacuated via the outlet 30 to a pressure of 0.2 torr or less, preferably less than 100 microns. The furnace 16 is then employed to provide a temperature in the reaction zone 14 in excess of 900° C., preferably about 1000° C.

The starting material 18 is then heated, by the furnace 22, in a manner which provides a residence time in the reaction zone 14 of about 1/10 of a second. Such vapor thus flows through the zone 14 to the receiving vessel 24, whereupon the cooling means 26 causes the condensation of the end product 28 therewithin.

The following specific examples further detail the process of the present invention.

EXAMPLE ONE 450 mg of o-xylene was preheated and vaporized in an apparatus, similar to that identified by the reference numeral 10 in FIG. 1, which had been evacuated to a pressure of about 0.075 mm Hg. The flask containing the o-xylene was heated to about 25° C. to provide a flow rate of about 0.01 g per minute through a one-inch diameter (OD) quartz tube, which had been heated to a temperature of 1,000° C. The total amount of vapor passed through the reaction zone in about ninety minutes and formed a liquid in a condensing flask which was cooled by liquid nitrogen. This liquid contained:

| benzene | 17.0% |
|---|---|
| toluene | 26.6% |
| p-xylene | 2.9% |
| styrene | 43.1% |
| o-xylene | 8.9% |

EXAMPLE TWO

The same apparatus and conditions described above with regard to Example One were employed to thermolyze 500 mg of m-xylene at a temperature of 1,000° C. at a pressure of 0.075 mm Hg, affording 402.5 mg of liquid products (80.5% recovery). The product distribution was:

| m-xylene | 66.2% |
|---|---|
| styrene | 23.8% |

EXAMPLE THREE

The same apparatus as that described in Example One was employed to thermolyze 650 mg of p-xylene, affording 533.6 mg of liquid products (82.1% recovery) with a product distribution of:

| p-xylene | 61.0% |
|---|---|
| styrene | 29.0% |

EXAMPLE FOUR 85 mg of benzocyclobutene was thermolyzed at 930° C. at 100 microns pressure in a procedure similar to that described in Example One, although a 0.5 inch (OD) quartz tube was employed as a reaction zone. This procedure afforded 70 mg of liquid product (73.7% recovery) which was 98% styrene.

EXAMPLE FIVE

A 0.5 inch (OD) quartz tube, packed with quartz chips, was employed for the thermolysis of 242 mg of p-cymene. The starting material was evaporated through the quartz tube under a vacuum (0.1 mg Hg) with a hot zone temperature of 930° C., affording 181.5 mg of liquid product (75% recovery). The product distribution was:

| benzene | 1.9% |
|---|---|
| toluene | 2.3% |
| ethylbenzene | 0.3% |
| p-xylene | 0.6% |
| styrene | 10.0% |
| p-methylstyrene | 63.7% |

EXAMPLE SIX

The 0.5 inch quartz tube packed with quartz chips described in Example Five was employed to thermolyze 200 mg of cumene, affording 150 mg of liquid product (75.5% recovery). The product distribution was:

| benzene | 15.1% |
|---|---|
| toluene | 4.2% |
| p-xylene | 0.4% |
| cumene | 9.6% |
| styrene | 55.5% |
| alpha-methylstyrene | 7.6% |

EXAMPLE SEVEN

The packed tube described in Example Five was then used to thermolyze 140 mg of p-ethyltoluene, affording 100 mg of liquid product (71.4% recovery), with a product distribution as follows:

| benzene | 1.2% |
|---|---|
| toluene | 3.8% |
| ethylbenzene | 2.3% |
| p-xylene | 23.8% |
| p-ethyltoluene | 11.0% |
| styrene | 16.0% |
| p-methylstyrene | 37.7% |

It will be appreciated that the process of the present invention provides an efficient process for the conversion of available $C_8$ and $C_9$ aromatics to useful monomers such as styrene and p-methylstyrene. For example, ortho-xylene is plentiful in many parts of the world as a byproduct of Dacron production, and other forms of xylene are also available at low cost. The production of styrene from xylenes is a reaction which has been difficult to achieve in comparison to the isopropyl benzene to styrene reaction due, in part, to the ease of removal of a methyl from the isopropyl group as opposed to removal of hydrogen from the methyl group in the former reaction. In addition, processes for the conversion of p-cymene to p-methylstyrene, benzocyclobutene to styrene, and ethyltoluene to styrene and p-methylstyrene are similarly unreported and advantageously adapted to the process of the present invention.

While the invention has been described in some detail by way of illustration and example, changes in form and the substitution of equivalents are contemplated as circumstances may suggest or render expedient. Although specific terms have been employed herein, they are intended in a descriptive sense and not for purposes of limitation, the scope of the invention being delineated in the following claims.

What is claimed is:

1. A process for the production of a polymerizable styrene, which comprises the gas-phase thermolysis, in the absence of a dehydrogenation catalyst, of an aromatic compound having the formula:

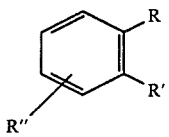

in the presence of an oxygen pressure in an amount of at least 0.2 torr up to about 5% of the aromatic compound, wherein R is alkyl, hydroxyalkyl or alkylhalide; R' is H, alkyl, hydroxyalkyl, or alkylhalide, or where R and R' together form cyclobutene; and R" is H or alkyl.

2. The process of claim 1 wherein R is methyl or isopropyl; R' is H or methyl, or where R and R' taken together are cyclobutene; and R" is H, methyl or ethyl.

3. A process for the production of styrene, which comprises subjecting xylene to gas-phase thermolysis at a temperature of at least 900° C. in the presence of an oxygen pressure of from about 0.2 torr up to less than about 5% of the xylene, in the absence of a dehydrogenation catalyst.

4. A process for the production of styrene, which comprises subjecting xylene to gas-phase thermolysis at a temperature of at least about 800° C. in admixture with an inert diluent in the presence of an oxygen pressure of from about 0.2 torr up to about 5% of the xylene, in the absence of a dehydrogenation catalyst.

5. The process of claim 4 wherein the inert diluent is steam.

6. A process for the production of p-methylstyrene from p-ethyltoluene, which comprises subjecting p-ethyltoluene to gas-phase thermolysis at a temperature of at least 900° C. in the presence of an oxygen pressure of from about 0.2 torr up to about 5% of the p-ethyltoluene, in the absence of a dehydrogenation catalyst.

7. A process for the production of p-methylstyrene which comprises subjecting p-ethyltoluene to gas-phase thermolysis at a temperature of at least 800° C. in admixture with an inert diluent, in the presence of an oxygen pressure from about 0.2 torr up to about 5% of the p-ethyltoluene, in the essential absence of a dehydrogenation catalyst.

* * * * *